(12) United States Patent
Sartor

(10) Patent No.: US 8,241,278 B2
(45) Date of Patent: *Aug. 14, 2012

(54) LAPAROSCOPIC APPARATUS FOR PERFORMING ELECTROSURGICAL PROCEDURES

(75) Inventor: Joe D. Sartor, Longmont, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/097,342

(22) Filed: Apr. 29, 2011

(65) Prior Publication Data

US 2011/0202056 A1 Aug. 18, 2011

Related U.S. Application Data

(63) Continuation of application No. 11/299,468, filed on Dec. 12, 2005, now Pat. No. 7,947,039.

(51) Int. Cl.
*A61B 18/14* (2006.01)
(52) U.S. Cl. .......... 606/42; 604/35; 606/45; 606/49
(58) Field of Classification Search .......... 606/34, 606/37, 38, 42, 45, 49; 604/35
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,693,106 A | 6/1951 | Henry |
| 2,827,056 A | 3/1958 | Degelman |
| 2,849,611 A | 8/1958 | Adams |
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |

(Continued)

FOREIGN PATENT DOCUMENTS

DE 179607 3/1905

(Continued)

OTHER PUBLICATIONS

U.S. Appl. No. 10/406,690, filed Apr. 3, 2003, Robert J. Behnke, II.

(Continued)

*Primary Examiner* — Lee S Cohen

(57) ABSTRACT

A system and apparatus for irrigating a surgical site during an electrosurgical procedure are disclosed. The system includes a hand piece having an elongated housing connected to a multi-lumen tube extending proximally from the housing and having an irrigation tube for delivering irrigation fluid, a suction tube for withdrawing irrigation fluid, and electrical wiring, a first controls for adjusting flow of irrigation fluid within the irrigation tube and second controls for adjusting flow of irrigation fluid within the suction tube. A valve cassette is connected to the multi-lumen tube, which includes an irrigation valve configured to control the flow within the irrigation tube and a suction valve configured to control the flow within the suction tube. A hardware control module controls the irrigation valve and the suction valve based on control signals from the first and second controls.

12 Claims, 5 Drawing Sheets

U.S. PATENT DOCUMENTS

| | | |
|---|---|---|
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gosner |
| 4,247,815 A | 1/1981 | Larsen et al. |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |

| | | | | | | |
|---|---|---|---|---|---|---|
| 4,862,889 A | 9/1989 | Feucht | | 5,354,325 A | 10/1994 | Chive et al. |
| 4,887,199 A | 12/1989 | Whittle | | 5,364,392 A | 11/1994 | Warner et al. |
| 4,890,610 A | 1/1990 | Kirwan et al. | | 5,369,567 A | 11/1994 | Furuta et al. |
| 4,903,696 A | 2/1990 | Stasz et al. | | 5,370,645 A | 12/1994 | Klicek et al. |
| 4,907,589 A | 3/1990 | Cosman | | 5,370,672 A | 12/1994 | Fowler et al. |
| 4,922,210 A | 5/1990 | Flachenecker et al. | | 5,370,675 A | 12/1994 | Edwards et al. |
| 4,925,089 A | 5/1990 | Chaparro et al. | | 5,372,596 A | 12/1994 | Klicek et al. |
| 4,931,047 A | 6/1990 | Broadwin et al. | | 5,383,874 A | 1/1995 | Jackson |
| 4,931,717 A | 6/1990 | Gray et al. | | 5,383,876 A | 1/1995 | Nardella |
| 4,938,761 A | 7/1990 | Ensslin | | 5,383,917 A | 1/1995 | Desai et al. |
| 4,942,313 A | 7/1990 | Kinzel | | 5,385,148 A | 1/1995 | Lesh et al. |
| 4,959,606 A | 9/1990 | Forge | | 5,396,194 A | 3/1995 | Williamson et al. |
| 4,961,047 A | 10/1990 | Carder | | 5,400,267 A | 3/1995 | Denen et al. |
| 4,961,435 A | 10/1990 | Kitagawa et al. | | 5,403,311 A | 4/1995 | Abele et al. |
| 4,966,597 A | 10/1990 | Cosman | | 5,403,312 A | 4/1995 | Yates et al. |
| 4,969,885 A | 11/1990 | Farin | | 5,409,000 A | 4/1995 | Imran |
| 4,992,719 A | 2/1991 | Harvey | | 5,409,485 A | 4/1995 | Suda |
| 4,993,430 A | 2/1991 | Shimoyama et al. | | 5,413,573 A | 5/1995 | Koivukangas |
| 4,995,877 A | 2/1991 | Ams et al. | | 5,414,238 A | 5/1995 | Steigerwald et al. |
| 5,015,227 A | 5/1991 | Broadwin et al. | | 5,417,719 A | 5/1995 | Hull et al. |
| 5,024,668 A | 6/1991 | Peters et al. | | 5,422,567 A | 6/1995 | Matsunaga |
| 5,044,977 A | 9/1991 | Vindigni | | 5,422,926 A | 6/1995 | Smith et al. |
| 5,057,105 A | 10/1991 | Malone et al. | | 5,423,808 A | 6/1995 | Edwards et al. |
| 5,067,953 A | 11/1991 | Feucht | | 5,423,809 A | 6/1995 | Klicek |
| 5,075,839 A | 12/1991 | Fisher et al. | | 5,423,810 A | 6/1995 | Goble et al. |
| 5,078,153 A | 1/1992 | Nordlander et al. | | 5,423,811 A | 6/1995 | Imran et al. |
| 5,087,257 A | 2/1992 | Farin et al. | | 5,425,704 A | 6/1995 | Sakurai et al. |
| 5,099,840 A | 3/1992 | Goble et al. | | 5,429,596 A | 7/1995 | Arias et al. |
| 5,103,804 A | 4/1992 | Abele et al. | | 5,430,434 A | 7/1995 | Lederer et al. |
| 5,108,389 A | 4/1992 | Cosmescu | | 5,432,459 A | 7/1995 | Thompson |
| 5,108,391 A | 4/1992 | Flachenecker | | 5,433,739 A | 7/1995 | Sluijter et al. |
| 5,113,116 A | 5/1992 | Wilson | | 5,436,566 A | 7/1995 | Thompson |
| 5,119,284 A | 6/1992 | Fisher et al. | | 5,438,302 A | 8/1995 | Goble |
| 5,122,137 A | 6/1992 | Lennox | | 5,443,462 A | 8/1995 | Hannant |
| 5,133,711 A | 7/1992 | Hagen | | 5,443,463 A | 8/1995 | Stern et al. |
| 5,151,102 A | 9/1992 | Kamiyama et al. | | 5,445,635 A | 8/1995 | Denen |
| 5,152,762 A | 10/1992 | McElhenney | | 5,445,638 A | 8/1995 | Rydell et al. |
| 5,157,603 A | 10/1992 | Scheller et al. | | 5,448,466 A | 9/1995 | Erckert |
| 5,160,334 A | 11/1992 | Billings et al. | | 5,451,224 A | 9/1995 | Goble et al. |
| 5,161,893 A | 11/1992 | Shigezawa et al. | | 5,452,725 A | 9/1995 | Martenson |
| 5,167,658 A | 12/1992 | Ensslin | | 5,454,809 A | 10/1995 | Janssen |
| 5,167,659 A | 12/1992 | Ohtomo et al. | | 5,458,597 A | 10/1995 | Edwards et al. |
| 5,190,517 A | 3/1993 | Zieve et al. | | 5,462,521 A | 10/1995 | Brucker et al. |
| 5,196,008 A | 3/1993 | Kuenecke | | 5,472,441 A | 12/1995 | Edwards et al. |
| 5,196,009 A | 3/1993 | Kirwan, Jr. | | 5,472,443 A | 12/1995 | Cordis et al. |
| 5,201,900 A | 4/1993 | Nardella | | 5,474,464 A | 12/1995 | Drewnicki |
| 5,207,691 A | 5/1993 | Nardella | | 5,480,399 A | 1/1996 | Hebborn |
| 5,216,338 A | 6/1993 | Wilson | | 5,483,952 A | 1/1996 | Aranyi |
| 5,230,623 A | 7/1993 | Guthrie et al. | | 5,485,312 A | 1/1996 | Horner et al. |
| 5,233,515 A | 8/1993 | Cosman | | 5,496,312 A | 3/1996 | Klicek |
| 5,234,427 A | 8/1993 | Ohtomo et al. | | 5,496,313 A | 3/1996 | Gentelia et al. |
| 5,244,462 A | 9/1993 | Delahuerga et al. | | 5,496,314 A | 3/1996 | Eggers |
| 5,249,121 A | 9/1993 | Baum et al. | | 5,498,261 A | 3/1996 | Strul |
| 5,249,585 A | 10/1993 | Turner et al. | | 5,500,012 A | 3/1996 | Brucker et al. |
| 5,254,117 A | 10/1993 | Rigby et al. | | 5,500,616 A | 3/1996 | Ochi |
| RE34,432 E | 11/1993 | Bertrand | | 5,511,993 A | 4/1996 | Yamada et al. |
| 5,267,994 A | 12/1993 | Gentelia et al. | | 5,514,129 A | 5/1996 | Smith |
| 5,267,997 A | 12/1993 | Farin | | 5,520,684 A | 5/1996 | Imran |
| 5,271,413 A | 12/1993 | Dalamagas et al. | | 5,531,774 A | 7/1996 | Schulman et al. |
| 5,281,213 A | 1/1994 | Milder et al. | | 5,534,018 A | 7/1996 | Wahlstrand et al. |
| 5,282,840 A | 2/1994 | Hudrlik | | 5,536,267 A | 7/1996 | Edwards et al. |
| 5,290,283 A | 3/1994 | Suda | | 5,540,677 A | 7/1996 | Sinofsky |
| 5,295,857 A | 3/1994 | Toly | | 5,540,681 A | 7/1996 | Strul et al. |
| 5,300,068 A | 4/1994 | Rosar et al. | | 5,540,682 A | 7/1996 | Gardner et al. |
| 5,300,070 A | 4/1994 | Gentelia | | 5,540,683 A | 7/1996 | Ichikawa |
| 5,304,917 A | 4/1994 | Somerville | | 5,540,684 A | 7/1996 | Hassler, Jr. |
| 5,318,563 A | 6/1994 | Malis et al. | | 5,541,376 A | 7/1996 | Ladtkow et al. |
| 5,323,778 A | 6/1994 | Kandarpa et al. | | 5,545,161 A | 8/1996 | Imran |
| 5,324,283 A | 6/1994 | Heckele | | 5,556,396 A | 9/1996 | Cohen et al. |
| 5,330,518 A | 7/1994 | Neilson et al. | | 5,558,671 A | 9/1996 | Yates |
| 5,334,183 A | 8/1994 | Wuchinich | | 5,559,688 A | 9/1996 | Pringle |
| 5,334,193 A | 8/1994 | Nardella | | 5,562,720 A | 10/1996 | Stern et al. |
| 5,341,807 A | 8/1994 | Nardella | | 5,569,242 A | 10/1996 | Lax et al. |
| 5,342,356 A | 8/1994 | Ellman | | 5,571,147 A | 11/1996 | Sluijter et al. |
| 5,342,357 A | 8/1994 | Nardella | | 5,573,533 A | 11/1996 | Strul |
| 5,342,409 A | 8/1994 | Mullett | | 5,584,830 A | 12/1996 | Ladd et al. |
| 5,346,406 A | 9/1994 | Hoffman et al. | | 5,588,432 A | 12/1996 | Crowley |
| 5,346,491 A | 9/1994 | Oertli | | 5,596,466 A | 1/1997 | Ochi |
| 5,348,554 A | 9/1994 | Imran et al. | | 5,596,995 A | 1/1997 | Sherman et al. |

| Patent No. | Date | Name |
|---|---|---|
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,935,124 A | 8/1999 | Klumb et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,780 A | 5/2000 | Gough et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,089,864 A | 7/2000 | Buckner et al. |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,104,248 A | 8/2000 | Carver |
| 6,106,524 A | 8/2000 | Eggers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,139,349 A | 10/2000 | Wright |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |

| Patent | Date | Inventor |
|---|---|---|
| 6,165,173 A | 12/2000 | Kamdar et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,270,497 B1 | 8/2001 | Sekino et al. |
| 6,273,886 B1 | 8/2001 | Edwards |
| 6,275,786 B1 | 8/2001 | Daners |
| 6,287,304 B1 | 9/2001 | Eggers et al. |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,304,138 B1 | 10/2001 | Johnson |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |
| 6,341,981 B1 | 1/2002 | Gorman |
| 6,350,262 B1 | 2/2002 | Ashley |
| 6,358,245 B1 | 3/2002 | Edwards |
| 6,364,877 B1 | 4/2002 | Goble et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,424,186 B1 | 7/2002 | Quimby et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,469,481 B1 | 10/2002 | Tateishi |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wardell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |

| | | |
|---|---|---|
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,190,933 B2 | 3/2007 | DeRuijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |

| | | |
|---|---|---|
| 7,517,351 B2 | 4/2009 | Culp et al. |
| 7,525,398 B2 | 4/2009 | Nishimura et al. |
| 7,568,619 B2 | 8/2009 | Todd et al. |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,864,129 B2 | 1/2011 | Konishi |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 2002/0029036 A1 | 3/2002 | Goble et al. |
| 2003/0153908 A1 | 8/2003 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0133189 A1 | 7/2004 | Sakurai |
| 2004/0172016 A1 | 9/2004 | Bek et al. |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0131390 A1 | 6/2005 | Heinrich et al. |
| 2006/0015095 A1 | 1/2006 | Desinger et al. |
| 2006/0079774 A1 | 4/2006 | Anderson |
| 2006/0111711 A1 | 5/2006 | Goble |
| 2006/0161148 A1 | 7/2006 | Behnke |
| 2006/0224152 A1 | 10/2006 | Behnke et al. |
| 2006/0291178 A1 | 12/2006 | Shih |
| 2007/0038209 A1 | 2/2007 | Buysse et al. |
| 2007/0088413 A1 | 4/2007 | Weber et al. |
| 2007/0093801 A1 | 4/2007 | Behnke |
| 2007/0129716 A1 | 6/2007 | Daw et al. |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2007/0293858 A1 | 12/2007 | Fischer |
| 2008/0004619 A1 | 1/2008 | Malis et al. |
| 2008/0015563 A1 | 1/2008 | Hoey et al. |
| 2008/0015564 A1 | 1/2008 | Wham et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0119843 A1 | 5/2008 | Morris |
| 2008/0125767 A1 | 5/2008 | Blaha |
| 2008/0132893 A1 | 6/2008 | D'Amelio et al. |
| 2008/0177199 A1 | 7/2008 | Podhajsky |
| 2008/0188849 A1 | 8/2008 | Goldberg et al. |
| 2008/0203997 A1 | 8/2008 | Foran et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2008/0287943 A1 | 11/2008 | Weber et al. |
| 2009/0018536 A1 | 1/2009 | Behnke |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2009/0234350 A1 | 9/2009 | Behnke et al. |
| 2009/0237169 A1 | 9/2009 | Orszulak |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0254077 A1 | 10/2009 | Craig |
| 2009/0259224 A1 | 10/2009 | Wham et al. |
| 2009/0292283 A1 | 11/2009 | Odom |
| 2009/0299360 A1 | 12/2009 | Ormsby |
| 2009/0306648 A1 | 12/2009 | Podhajsky et al. |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0079215 A1 | 4/2010 | Brannan et al. |
| 2010/0082022 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0179529 A1 | 7/2010 | Podhajsky et al. |
| 2010/0179533 A1 | 7/2010 | Podhajsky |
| 2010/0179534 A1 | 7/2010 | Podhajsky et al. |
| 2010/0179535 A1 | 7/2010 | Podhajsky et al. |
| 2010/0179536 A1 | 7/2010 | Podhajsky et al. |
| 2010/0179538 A1 | 7/2010 | Podhajsky |
| 2010/0179541 A1 | 7/2010 | Joseph et al. |
| 2010/0179542 A1 | 7/2010 | Joseph et al. |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0318079 A1 | 12/2010 | McPherson et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0202056 A1 | 8/2011 | Sartor |
| 2011/0204903 A1 | 8/2011 | Gilbert |
| 2011/0208179 A1 | 8/2011 | Prakash et al. |
| 2011/0213354 A1 | 9/2011 | Smith |
| 2011/0213355 A1 | 9/2011 | Behnke, II |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 640317 | 3/1995 |
| EP | 694291 | 1/1996 |
| EP | 617925 | 7/1996 |
| EP | 836868 | 4/1998 |
| EP | 878169 | 11/1998 |
| EP | 882955 | 12/1998 |
| EP | 1051948 | 11/2000 |
| EP | 1053720 | 11/2000 |
| EP | 1151725 | 11/2001 |
| EP | 1278007 | 1/2003 |
| EP | 1293171 | 3/2003 |
| EP | 1472984 | 11/2004 |
| EP | 1495712 | 1/2005 |
| EP | 1500378 | 1/2005 |
| EP | 1146827 | 3/2005 |
| EP | 1535581 | 6/2005 |
| EP | 870473 | 9/2005 |
| EP | 1609430 | 12/2005 |
| EP | 1366724 | 1/2006 |
| EP | 1707144 | 3/2006 |
| EP | 1645235 | 4/2006 |
| EP | 880220 | 6/2006 |
| EP | 1681026 | 7/2006 |
| EP | 1707143 | 10/2006 |
| EP | 1744354 | 1/2007 |
| EP | 1776929 | 4/2007 |
| EP | 1810628 | 7/2007 |
| EP | 1810630 | 7/2007 |
| EP | 1810631 | 7/2007 |
| EP | 1810632 | 7/2007 |
| EP | 1810633 | 7/2007 |
| EP | 1810634 | 7/2007 |
| EP | 1854423 | 11/2007 |
| EP | 1862137 | 12/2007 |
| EP | 2025297 | 5/2008 |
| EP | 1263181 | 9/2008 |
| EP | 2253286 | 11/2010 |
| EP | 1594392 | 6/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2154881 | 9/1985 |
| GB | 2164473 | 3/1986 |
| GB | 2214430 | 9/1989 |
| GB | 2331247 | 5/1999 |
| GB | 2358934 | 8/2001 |
| GB | 2434872 | 8/2007 |
| SU | 166452 | 1/1965 |
| SU | 727201 | 4/1980 |
| WO | WO92/06642 | 4/1992 |
| WO | WO92/07622 | 5/1992 |
| WO | WO93/24066 | 12/1993 |
| WO | WO94/10922 | 5/1994 |
| WO | WO94/24949 | 11/1994 |
| WO | WO94/28809 | 12/1994 |
| WO | WO95/09577 | 4/1995 |
| WO | WO95/18575 | 7/1995 |
| WO | WO95/19148 | 7/1995 |
| WO | WO95/25471 | 9/1995 |
| WO | WO95/25472 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39085 | 12/1996 |
| WO | WO96/39086 | 12/1996 |
| WO | WO96/39088 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/10763 | 3/1997 |
| WO | WO97/11648 | 4/1997 |
| WO | WO97/17029 | 5/1997 |
| WO | WO97/43971 | 11/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO99/56647 | 11/1999 |
| WO | WO00/48672 | 8/2000 |
| WO | WO00/54683 | 9/2000 |
| WO | WO01/01847 | 1/2001 |
| WO | WO02/00129 | 1/2002 |
| WO | WO02/11634 | 2/2002 |
| WO | WO02/32333 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/047446 | 6/2003 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/043240 | 5/2004 |
| WO | WO2004/047659 | 6/2004 |
| WO | WO2004/052182 | 6/2004 |
| WO | WO2004/073488 | 9/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060849 | 7/2005 |
| WO | WO2005/115235 | 12/2005 |
| WO | WO2005/117735 | 12/2005 |
| WO | WO2006/050888 | 5/2006 |
| WO | WO2006/105121 | 10/2006 |
| WO | WO2007/055491 | 5/2007 |

| WO | WO2007/067522 | 6/2007 |
| WO | WO2007/105963 | 9/2007 |
| WO | WO2008/002517 | 1/2008 |
| WO | WO2008/003058 | 1/2008 |
| WO | WO2008/011575 | 1/2008 |
| WO | WO2008/043999 | 4/2008 |
| WO | WO2008/044000 | 4/2008 |
| WO | WO2008/044013 | 4/2008 |
| WO | WO2008/053532 | 5/2008 |
| WO | WO2008/070562 | 6/2008 |
| WO | WO2008/071914 | 6/2008 |
| WO | WO2008/110756 | 9/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. Ml, Jan. Mar. 1964, pp. 16-27.
Cosman et al, "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.

International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Japanese Office Action for Application No. 2006-335033 dated Sep. 9, 2011.
US 6,878,148, 04/2005, Goble et al. (withdrawn)

LAPAROSCOPIC APPARATUS FOR PERFORMING ELECTROSURGICAL PROCEDURES

CROSS-REFERENCE TO RELATED APPLICATION

The present application is a continuation of U.S. patent application Ser. No. 11/299,468 filed on Dec. 12, 2005 by Joe D. Sartor now U.S. Pat. No. 7,947,039, the entire contents of which is incorporated by reference herein.

BACKGROUND

1. Technical Field

The present disclosure relates generally to an apparatus and method for performing laparoscopic electrosurgical procedures, and more particularly, to an apparatus for controlling suction and irrigation cycles during laparoscopic electrosurgical procedures.

2. Background of Related Art

During electrosurgery, a source or active electrode delivers energy, such as radio frequency (RF) energy, from an electrosurgical generator to a patient and a return electrode or a plurality thereof carry current back to the electrosurgical generator. In monopolar electrosurgery, the source electrode is typically a hand-held instrument placed by the surgeon at the surgical site and the high current density flow at this electrode creates the desired surgical effect of ablating, cutting or coagulating tissue. The patient return electrodes are placed at a remote site from the source electrode and are typically in the form of pads adhesively adhered to the patient.

Bipolar electrosurgery is conventionally practiced using electrosurgical forceps-type device, where the active and return electrodes are housed within opposing forceps' jaws. The return electrode is placed in close proximity to the active (i.e., current supplying) electrode such that an electrical circuit is formed between the two electrodes (e.g., electrosurgical forceps). In this manner, the applied electrical current is limited to the body tissue positioned between the electrodes.

During electrosurgical procedures, byproducts form at the surgical site from coagulated and/or cut flesh (e.g., debris, smoke, etc.). This debris may be removed by irrigating the site, where an irrigation fluid is supplied to the surgical site and then withdrawn through suction. Conventional irrigation mechanisms have been controlled mechanically with the mechanical controls disposed within a handle holding the electrosurgical instrument. Such designs could not achieve a desired level of suction and/or irrigation and moreover, these designs were not compact and ergonomic.

Therefore, there is a need for an electrosurgical apparatus having an irrigation system controlled through electrical means and disposed outside the apparatus' handle.

SUMMARY

The present disclosure provides for a system and apparatus for irrigating a surgical site during an electrosurgical procedure. The system includes a hand piece for controlling an electrosurgical generator and an irrigation system having an irrigation tube for supplying irrigation fluid and a suction tube for withdrawing irrigation fluid and smoke. The hand piece's controls are connected to a hardware module which controls irrigation and suction valves disposed within a valve cassette which adjusts the flow of the irrigation fluid and suction. In addition, the irrigation fluid is used to cool the electrode.

According to one embodiment of the present disclosure, a system for irrigating a surgical site during an electrosurgical procedure is provided. The system includes a hand piece having an elongated housing connected to a multilumen tube extending proximally from the housing and having an irrigation tube for delivering irrigation fluid, a suction tube for withdrawing irrigation fluid, and electrical wiring, the hand piece further includes first controls for adjusting flow of irrigation fluid within the irrigation tube and second controls for adjusting flow of irrigation fluid within the suction tube, the first and second controls transmitting first and second control signals through the electrical wiring; a valve cassette connected to the multilumen tube, the cassette including an irrigation valve configured to control the flow within the irrigation tube and a suction valve configured to control the flow within the suction tube, the irrigation tube further connected to an irrigation fluid source and the suction tube further connected to a vacuum source; and a hardware control module connected to the electrical wiring for receiving the first and second control signals and controlling the irrigation valve through an irrigation servo actuator based on the first control signals and controlling the suction valve through a suction servo actuator based on the second control signals.

According to another embodiment of the present disclosure, an apparatus for controlling irrigation at a surgical site during an electrosurgical procedure is provided. The apparatus includes an elongated housing, a multilumen tube extending proximally from the housing and having an irrigation tube for delivering irrigation fluid including an irrigation check valve, a suction tube for withdrawing irrigation fluid including a suction check valve, and electrical wiring, first and second controls configured for adjusting flow of irrigation fluid within the irrigation tube and for adjusting suction within the suction tube respectively, the first and second controls transmitting first and second control signals, the multilumen tube connected to a valve cassette, the cassette including an irrigation valve configured to control the flow within the irrigation tube and a suction valve configured to control the flow within the suction tube, the irrigation tube further connected to an irrigation fluid source and the suction tube further connected to a vacuum source, and a hardware control module configured to receive the first and second control signals and controlling the irrigation valve through an irrigation servo actuator based on the first control signals and controlling the suction valve through a suction servo actuator based on the second control signals.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
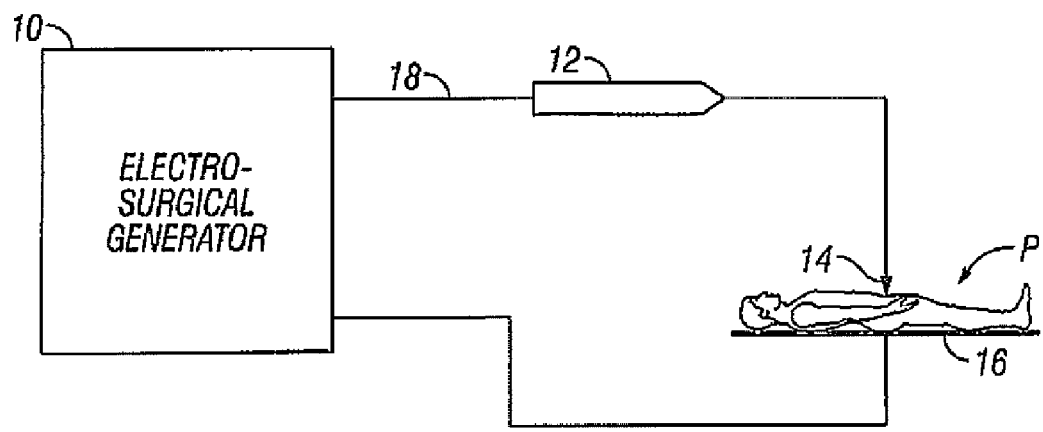
FIG. 1 is a block diagram illustrating in general an electrosurgical system according to an embodiment of the present disclosure.

Embodiments of the present disclosure are described below with reference to the accompanying drawings. In the following description, well-known functions or constructions are not described in detail to avoid obscuring the present disclosure in unnecessary detail.

The foregoing disclosure describes embodiments with reference to a monopolar laparoscopic surgical instrument. However, principles of the present disclosure may be utilized in a bipolar instrument as well as suitable open instruments.

An electrosurgical system and method to be used to perform cautery procedures, hemostatis, and other suitable procedures are provided. The system provides irrigation and/or suction (e.g., a vacuum line), which may be performed contemporaneously with the electrosurgical procedure or after the procedure is complete. In some embodiment, the irrigation fluid may be used to cool the electrosurgical cautery electrode to reduce eschar build-up, modify tissue effect, and/or prevent inadvertent burns from a heated electrode.

Embodiments of the presently disclosed electrosurgical system will now be described in detail with reference to the drawings wherein like reference numerals identify similar or identical elements. As used herein, the term "distal" refers to that portion that is further from the user while the term "proximal" refers to that portion that is closer to the user.

FIG. 1 shows an electrosurgical system including a generator 10, a hand piece 12 (e.g., an electrosurgical pencil) having an active electrode 14 at a distal end thereof which is brought in contact with a patient P to effect a cut and/or coagulation procedure depending upon the selected operating mode. The active electrode 14 is an electrically conducting element that is usually elongated and may be in the form of a thin flat blade with a pointed or rounded distal end. Alternatively, the active electrode 14 may include an elongated narrow cylindrical needle which is solid or hollow with a flat, rounded, pointed or slanted distal end.

Attached to the patient P is a return electrode 16 that returns the electrosurgical current from the patient P to the generator 10. The hand piece 12 is coupled to the generator 10 via a multilumen tube 18 extending from a proximal end of the hand piece 12. In one embodiment, the multilumen tube 18 includes electrical wires for supplying the electrosurgical energy to the active electrode 14 as well as electrical power for the controls of the hand piece 12.

The active electrode 14 may be used laparoscopically, e.g., inserted into a body cavity through a percutaneous incision. To accomplish this, the electrode 14 may be introduced into a body cavity through a suitable trocar (not shown). The trocar may include an elongated tube that penetrates the body cavity with its distal end and the electrode 14 is introduced thereto through its proximal end. In addition, the trocar may include a hemostatic valve disposed at its proximal end to prevent backflow of gases.

The hand piece 12 also includes an irrigation tip that irrigates the surgical site, the details of which will be described below. Other components of the irrigation system, such as irrigation fluid supply and valve mechanisms may be disposed within the generator 10 or within a separate stand-alone device such as a suitable cassette. The irrigation and suction lines are coupled from the irrigation system to the hand piece 12 and thereafter to the irrigation tip and may be included within the multilumen tube 18.

The irrigation system supplies a suitable irrigation fluid such as a saline solution, through the irrigation tip near the active electrode 14. The irrigation fluid is used to cool the active electrode 14 during electrosurgical usage to reduce or eliminate eschar (e.g., sloughed-off dead tissue caused by a burn or cauterization). In addition, the irrigation fluid may be used to remove any debris caused by the electrosurgical procedure.

Figure 2A:
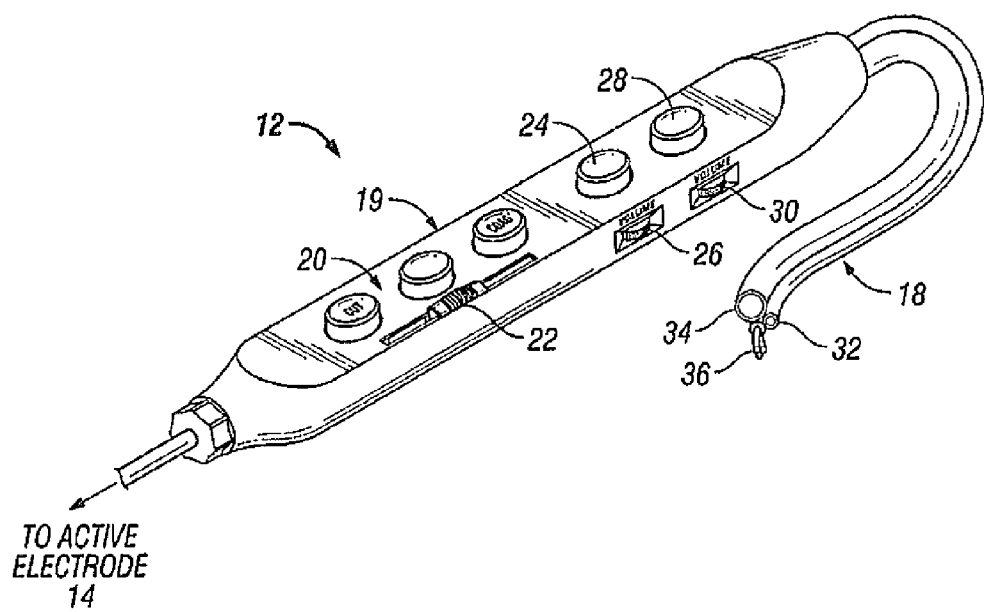
FIG. 2A is a perspective view of a hand piece in accordance with an embodiment of the present disclosure.

The hand piece 12 remains outside the body cavity and outside the trocar and allows the surgeon to control the electrosurgical operations as well as irrigation cycles. Referring to FIG. 2A, the hand piece 12 according to one embodiment of the disclosure is shown and includes a variety of controls within an elongated housing 19. The hand piece 12 includes mode selection controls 20 that allow the surgeon to select the operating mode for the generator 10 (e.g., cut, coagulation, blend). Generally, generators operate in a plurality of modes, e.g., cut, coagulation, or blend, accomplished by using different current waveforms. Using a constant waveform, a generator allows a surgeon to vaporize or cut tissue since a constant waveform produces heat very rapidly. Using an intermittent waveform causes a generator's duty cycle to be reduced to coagulate tissue. A blended current allows for a mixture of the two above waveforms to achieve intermediate results. The hand piece 12 also includes intensity controls 22 that allow the surgeon to modify the power of the energy being supplied to the active electrode 14, which is supported within the housing 19 and extends distally therefrom.

The hand piece 12 also includes controls for adjusting the irrigation system. More specifically, the hand piece 12 may include an irrigation controller 24 which activates and deactivates the flow of the irrigation fluid and an irrigation volume adjuster 26 which adjusts the flow volume of the irrigation fluid. In addition, the hand piece 12 includes a suction control 28 which activates and deactivates vacuum suction apparatus to withdraw the aspirated irrigation fluid. A suction volume adjuster 30 controls a setting level of the vacuum pump which controls the rate at which irrigation fluid is withdrawn.

The mode selection controls 20, intensity controls 22, irrigation volume adjuster 26 and suction volume adjuster 30 are operatively connected to a voltage divider network ("VDN") (e.g., a film-type potentiometer). For the purposes herein, the term "voltage divider network" relates to any suitable form of resistive, capacitive or inductive circuit that determines the output voltage across a voltage source (e.g., one of two impedances) connected in series. A "voltage divider" as used herein relates to a number of resistors connected in series which are provided with taps at certain points to make available a fixed or variable fraction of the applied voltage. An example of a hand piece employing such a voltage divider is discussed in a commonly-owned U.S. patent application Ser. No. 10/718,113 entitled "Electrosurgical Pencil With Improved Controls," which is hereby incorporated by reference in its entirety. It is also envisioned that the irrigation volume adjuster 26 and suction volume adjuster 30 divider networks may be aligned with a single slide (not explicitly shown) wherein moving of the slide in one direction adjusts flow of irrigation fluid and moving the slide in another direction adjusts flow of aspirated irrigation fluid.

The multilumen tube 18 extends proximally from the housing 19 and includes multiple lumens containing conduits for electrical wiring 36, an irrigation tube 32 that supplies the irrigation fluid to a surgical site, and suction tube 34 that withdraws the irrigation fluid by providing a conduit to a suitable vacuum source. The electrical wiring 36 includes wires for transmitting electrosurgical current to the active electrode 14 and control current for transmitting input signals from the controls of the hand piece 12. Using DC voltage to transmit input signals is well known in the art and is described in commonly owned U.S. Pat. Nos. 3,699,967 and 3,801,800, both of which are hereby incorporated by reference in their entirety.

Figure 2B:
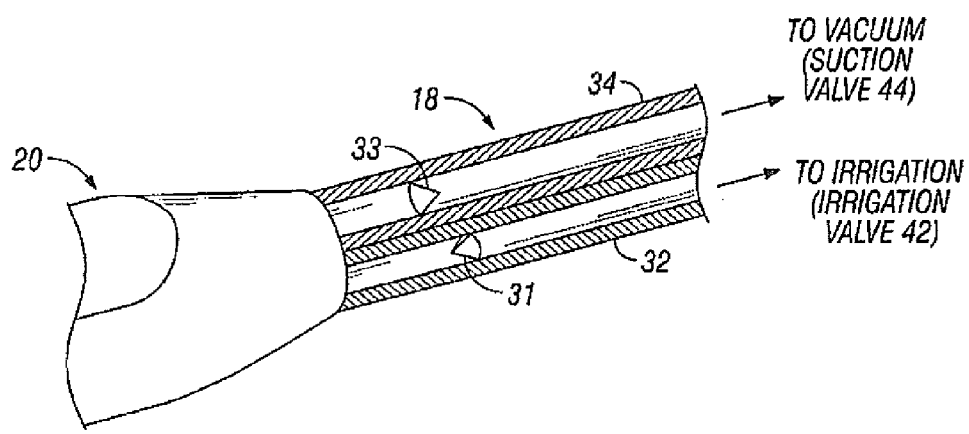
FIG. 2B is a cross-sectional perspective view of a tube extending from the hand piece of FIG. 2A.

As shown in FIG. 2B, an irrigation check valve 31 and a suction check valve 33 are disposed within the irrigation tube 32 and the suction tube 34, respectively, at the proximal end of the hand piece 12. The suction check valve 33 may be of "duck bill" design or in some embodiment may be a flap. Orientation of the suction check valve 33 allows fluids and vacuum to flow with minimum resistance therethrough but prevents fluid from draining in the opposing direction.

The irrigation check valve 31 may also be of "duck bill" design, as well as, a poppet, a flap, a spring-loaded ball type check valve, or any suitable check valve that may be inserted modularly into the irrigation tube. The irrigation check valve 31 is configured to open under sufficient opening pressure to allow for irrigation fluid to flow therethrough. Opening pressure from about 6 inches to about 48 inches of water column pressure is sufficient to prevent fluid in the irrigation tube 32 from draining through the hand piece 12 when an irrigation valve 42 is closed (see FIG. 3). The pressure is also sufficient to provide minimum resistance to flow pressure when the irrigation valve 42 is open.

Figure 3:
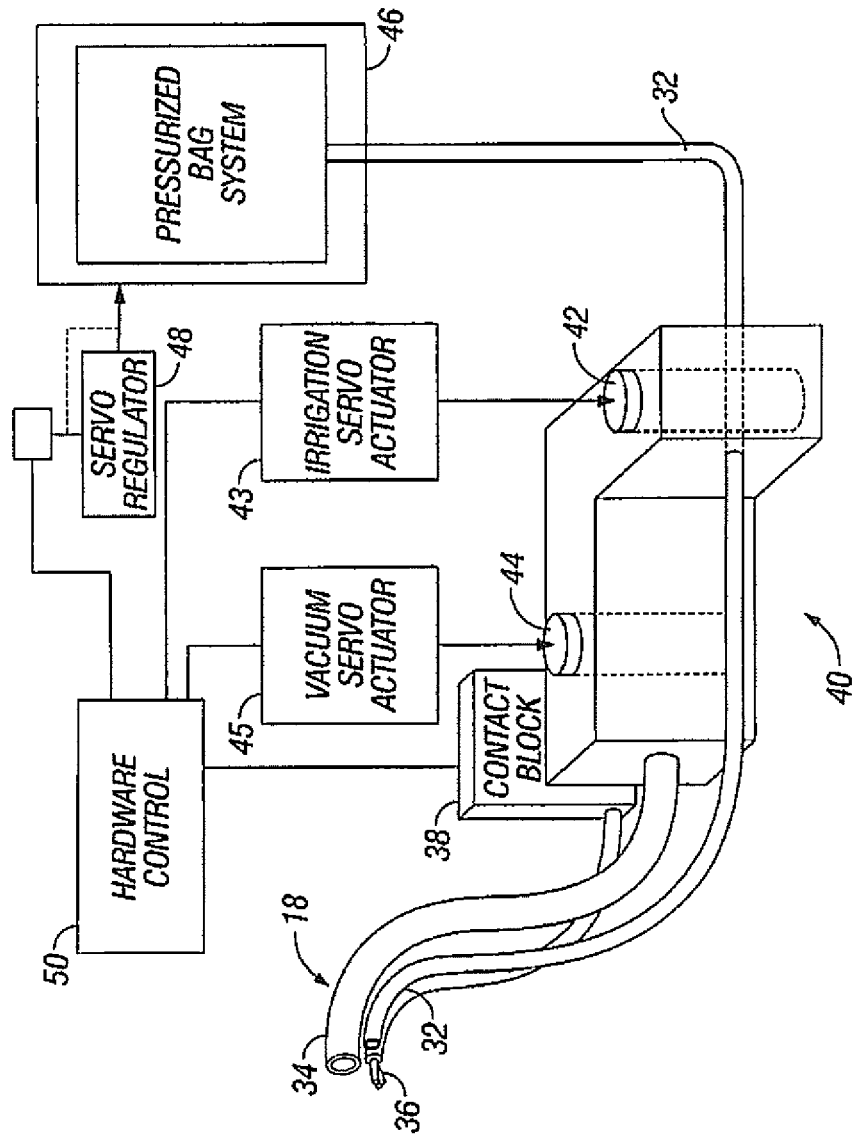
FIG. 3 is a block diagram of a valve cassette according to an embodiment of the present disclosure.

With reference to FIG. 3, the multilumen tube 18 couples the hand piece 12 to a valve cassette 40 that includes suitable mechanisms for controlling the in-flow and out-flow of the irrigation fluid at the surgical site. The electrical wiring 36 is coupled to a contact block 38 which provides an electrical interface between the hand piece 12 and the generator 10. More specifically, the contact block 38 is electrically coupled to a hardware control module 50 that monitors and controls the operation of the generator 10 and the valve cassette 40. The control module 50 may include electronic circuitry such as a microprocessor, memory, and comparators for performing a variety of functions within the purview of those skilled in the art (e.g., comparing values, receiving control signals, converting analog signals to and from digital signals, issuing control commands to generator 10 and valve cassette 40, etc.).

The valve cassette 40 includes a suction valve 44 which controls vacuum within the suction tube 34. Opening the suction valve 44 creates vacuum within the suction tube 34 by providing access to a vacuum pump (not explicitly shown) thereby leading to siphoning off of the aspirated irrigation fluid. Closing the suction valve 44 terminates access to the vacuum pump. Regulating the position of the suction valve 44 allows the surgeon to modulate the amount of suction.

The suction valve 44 may be regulated by a vacuum servo actuator 45 that opens and closes the valves based on control signals from the control module 50. The control signals originate from the suction control 28 and the suction volume adjuster 30 and are transmitted to the control module 50 along the electrical wiring 36 and through the contact block 38.

The valve cassette 40 also includes the irrigation valve 42 that adjusts the aperture of the irrigation tube 36, thereby adjusting the flow of the irrigation fluid to the surgical site.

The irrigation valve 42 may be controlled by an irrigation servo actuator 43 receives control signals from the control module 50. The irrigation fluid may be dispensed from a pressurized bag 46 that may be compressed by a servo regulator 48 (e.g., an air supply pump).

In one embodiment, flow of the irrigation fluid is regulated in the following manner. Initially, the surgeon selects desired pressure for supplying the irrigation fluid. Thereafter, control signals are transmitted from the irrigation controller 24 and the irrigation volume adjuster 26 through the electrical wiring 36 and the contact block 38. The desired flow/pressure may be achieved by increasing pressure on the pressurized bag 46 and leaving the irrigation valve 42 open. Alternatively, the pressure on the pressurized bag 46 may remain static and the irrigation valve 42 may be adjusted to achieve the desired flow rate. Those skilled in the art will appreciate that irrigation fluid may be stored in a variety of containers (e.g., a storage tank) and be dispensed using a pump. The pump may be controlled by varying the pump's pressure between zero and maximum setting, e.g., a variable speed pump. The irrigation volume adjuster 26 includes a VDN may delivers a control voltage to the pump varying its output pressure.

Figure 4A:
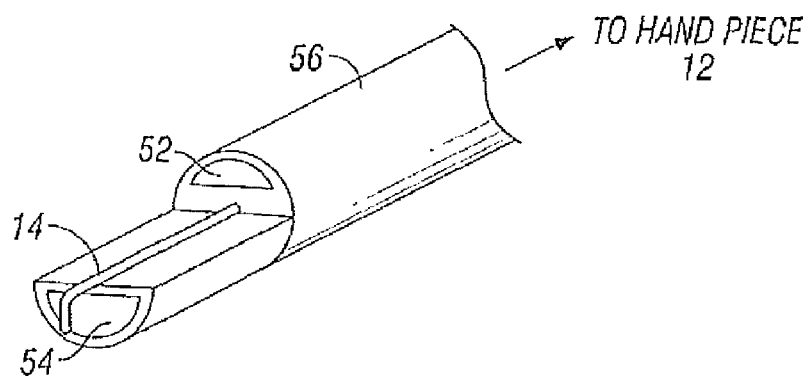
FIG. 4A is a perspective view of an active electrode with an irrigation tip according to one embodiment of the present disclosure.
Figure 4B:
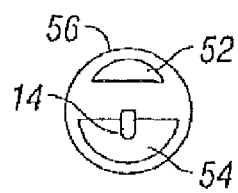
FIG. 4B is a frontal view of the active electrode with the irrigation tip of FIG. 4A.
Figure 4C:
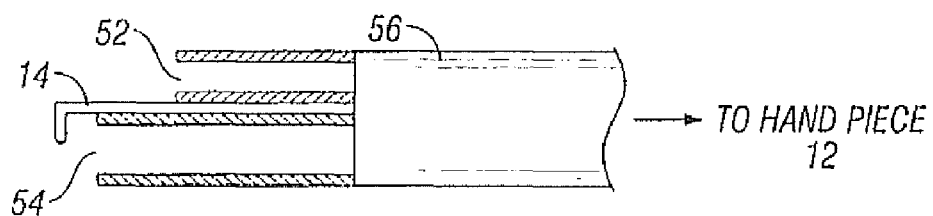
FIG. 4C is a cross sectional view of the active electrode with the irrigation tip of FIG. 4A.

FIGS. 4A-C show the active electrode 14 with an irrigation tip 56. The active electrode 14 is bent into an L-shaped configuration. However, the electrode 14 may be in a variety of suitable shapes and configurations (e.g., spatula, needle, ballpoint, solid, hollow, etc.). The active electrode 14 is positioned between an irrigation opening 52 and a suction opening 54 as shown in FIGS. 4A-C. In one embodiment, the irrigation tip 56 is made from an insulative material to prevent accidental shock to the patient.

It is envisioned that during an electrosurgical procedure the irrigation fluid passes through the irrigation opening 52 and into the surgical site to wash away any debris generated during the surgical procedure. The irrigation fluid is then suctioned off through the suction opening 54 to evacuate the debris from the surgical site. In addition, the smoke generated during the procedure is also evacuated. The irrigation tip 56 may have a plurality of irrigation openings 52 and suction openings 54.

The present invention also contemplates that the irrigation fluid is used to cool the active electrode 14 in order to maintain the tip of the electrode 14 at a temperature below that of eschar formation (e.g., 100° C.). The active electrode 14 may include specific geometry that improves heat transfer from the surface of the active electrode 14 to the irrigation fluid (e.g., grooves chiseled therein). To achieve efficient heat transfer from the active electrode 14, the irrigation fluid may be passed at a sufficiently slow rate so that the fluid flows along the active electrode 14 via capillary action and into the suction opening 54. The irrigation and suction openings 52, 54 extend for the same distance longitudinally to accommodate for irrigation of the active electrode 14.

It is also envisioned that the suction opening 54 may extend further than the irrigation opening 52. This arrangement allows the irrigation fluid to flow along a larger segment of the active electrode 14 than an arrangement where the irrigation and suction paths are approximately the same length. As a result, the active electrode 14 transfers more heat to the irrigation fluid. Such additional cooling may be utilized in electrosurgical procedures that have higher energy requirements, since such procedures generate more heat and require more cooling to alleviate eschar formation. In addition, extending the suction opening 54 allows for irrigation fluid to be jetted beyond the active electrode 14 allowing for better irrigation of the surgical site.

Figure 5A:
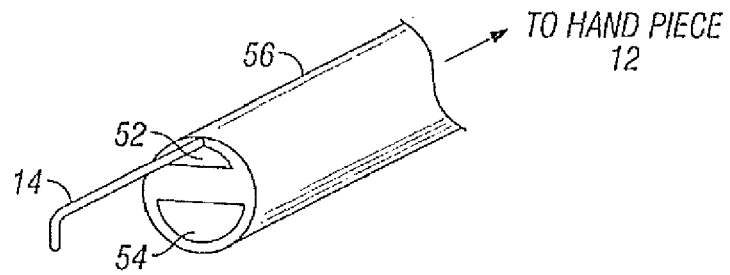
FIG. 5A is a perspective view of an active electrode with an irrigation tip according to another embodiment of the present disclosure.
Figure 5B:
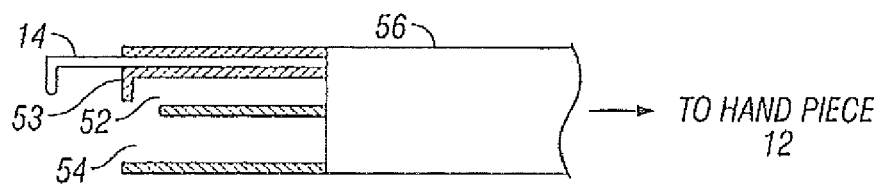
FIG. 5B is a cross sectional view of the active electrode with the irrigation tip of FIG. 5A.

FIGS. 5A-B show another embodiment of the active electrode 14 and the irrigation tip 56, where the active electrode 14 is positioned above the irrigation and suction openings 52, 54. This arrangement may be particularly useful where cooling of the electrode 14 is secondary to providing proper irrigation and evacuation of the debris and smoke from the surgical site. As shown in FIG. 5B, the irrigation opening 52 includes a lip 53 to direct the flow of the irrigation fluid downward and into the surgical site, which allows for rapid irrigation of the surgical site.

Figure 6A:
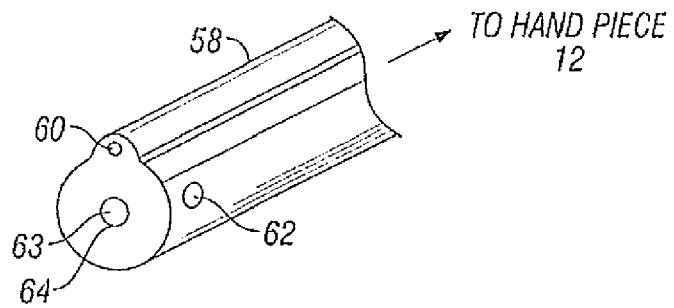
FIG. 6A is a perspective view of an irrigation tip according to a further embodiment of the present disclosure.
Figure 6B:
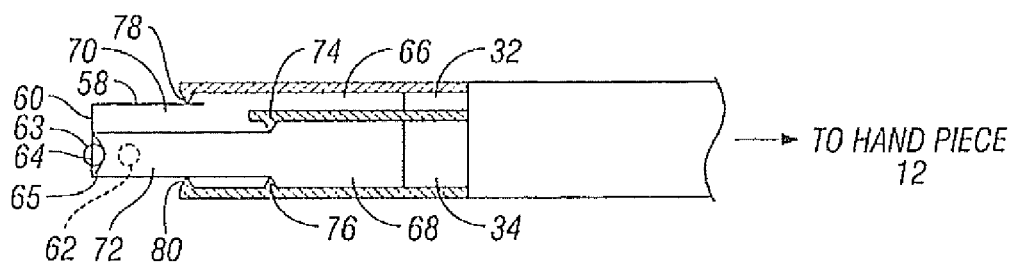
FIG. 6B is a cross sectional view of the irrigation tip of FIG. 6A.

FIGS. 6A-B show an irrigation adapter 58 without the active electrode 14. The irrigation adapter 58 includes an irrigation opening 60 and a front suction opening 64. The irrigation adapter 58 may include a ball 63 serving a ball valve 65, such as when the suction is on or the irrigation adapter 58 is pressed against a surface (e.g., tissue) the ball 63 retracts to allow for irrigation fluid to pass through the front suction opening 64. In addition, the irrigation adapter 58 also includes one or more side suction opening 62.

FIG. 6B shows a cross sectional view of the irrigation adapter 58 and its connectivity to the irrigation tube 32 and the suction tube 34. The irrigation fluid enters the irrigation adapter 58 through an irrigation passage 66 and flows through an irrigation channel 70 of the irrigation adapter 58. The irrigation fluid is extracted through a suction channel 72 and enters the suction tube 34 through a suction passage 68. The suction passage 72 extends further than the irrigation passage 70 to allow for separated and distinct in and out flow paths.

The irrigation adapter 58 is coupled to the irrigation and suction tubes by a plurality of ridges 74, 76, 78, 80. The ridges 74, 76 are in contact with the top and bottom outside surfaces of the suction passage 68 and the ridges 78, 80 are in contact with the top outside surface of the irrigation passage 70 and the suction passage 80, respectively. In effect, the ridges 78, 80 secure the entire irrigation adapter 58, while the ridges 78, 80 provide additional support to the suction passage 72 that extends beyond the length of the irrigation passage 70.

It is envisioned that the irrigation and suction system of the present disclosure may be utilized as a stand-alone system (e.g., not part of an electrosurgical apparatus). The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A system for irrigating a surgical site during an electrosurgical procedure, comprising:
    a hand piece having a housing with a multi-lumen tube extending therefrom and an electrode operatively associated therewith disposed in electrical communication with a generator, the multi-lumen tube including an irrigation tube configured to deliver irrigation fluid and a suction tube configured to withdraw irrigation fluid, the irrigation tube coupled to an irrigation fluid source and the suction tube coupled to a vacuum source, each of the irrigation tube and suction tube disposed in fluid communication with an irrigation tip having at least one outlet defined therein that supplies irrigation fluid and at least one inlet defined therein that withdraws irrigation fluid,
    wherein the at least one inlet is distal relative to the at least one outlet with respect to the irrigation tip, the disposition of the at least one inlet opening permitting irrigation fluid to flow along a larger segment of the electrode thereby maximizing the transfer of heat from the electrode to the irrigation fluid.

2. A system of claim 1, wherein the hand piece further includes first controls configured to adjust the flow of irrigation fluid within the irrigation tube, second controls configured to adjust suction within the suction tube and third controls configured to allow the selection of an operating mode of the generator.

3. A system of claim 1, further including a valve cassette coupled to the multi-lumen tube, the valve cassette including an irrigation valve configured to control the flow within the irrigation tube and a suction valve configured to control the flow within the suction tube.

4. A system of claim 3, wherein the handpiece includes electrical wiring configured to transmit electrosurgical energy from the generator to the electrode, the first and second controls transmitting first and second control signals through the electrical wiring.

5. A system of claim 4, wherein a hardware control module is coupled to the electrical wiring and configured to receive the first and second control signals and is operable to control the irrigation valve based on the first control signals and to control the suction valve based on the second control signals, wherein the hardware control module monitors and controls the operation of the generator and valve cassette.

6. A system of claim 1, wherein the irrigation source is a pressurized bag.

7. A system of claim 6, further comprising a servo regulator configured to adjust pressure within the pressurized bag.

8. A system of claim 1, wherein the irrigation fluid is delivered by a variable speed pump from the irrigation source.

9. An apparatus of claim 1, wherein the electrode is disposed between the at least one inlet opening and the at least one outlet opening.

10. An apparatus of claim 1, wherein the irrigation tip includes a ball valve disposed at the at least one inlet opening to selectively prevent irrigation fluid from flowing therethrough.

11. A system for irrigating a surgical site during an electrosurgical procedure, comprising:
    a generator;
    an electrode;
    a hand piece adapted to selectively couple to the generator and in operable communication with the electrode, the hand piece having a housing with a multi-lumen tube extending therefrom, the multi-lumen tube including an irrigation tube adapted to couple to a fluid source and a suction tube adapted to couple to a vacuum source; and
    an irrigation tip having at least one outlet defined therein that supplies irrigation fluid and at least one inlet defined therein that withdraws irrigation fluid while the electrode is active, the irrigation tip in fluid communication with each of the irrigation tube and suction tube, the at least one inlet is distal relative to the at least one outlet with respect to a distal tip of the irrigation tip, the disposition of the at least one inlet permitting irrigation fluid to flow along a larger segment of the electrode thereby maximizing the transfer of heat from the electrode to the irrigation fluid.

12. A system of claim 11, further including an irrigation fluid source in fluid communication with the irrigation tube for delivering irrigation fluid and a vacuum source in fluid communication with the suction tube for withdrawing irrigation fluid.

* * * * *